(12) United States Patent
Saegusa (10) Patent No.: US 11,519,838 B2
(45) Date of Patent: Dec. 6, 2022

(54) RIGIDITY CHARACTERISTICS MEASUREMENT DEVICE

(71) Applicant: PRGR Co., Ltd., Tokyo (JP)

(72) Inventor: Hiroshi Saegusa, Tokyo (JP)

(73) Assignee: The Yokohama Rubber Co., LTD., Tokyo (JP)

(*) Notice: Subject to any disclaimer, the term of this patent is extended or adjusted under 35 U.S.C. 154(b) by 51 days.

(21) Appl. No.: 16/636,318

(22) PCT Filed: Apr. 5, 2018

(86) PCT No.: PCT/JP2018/014572
§ 371 (c)(1),
(2) Date: Feb. 3, 2020

(87) PCT Pub. No.: WO2019/030973
PCT Pub. Date: Feb. 14, 2019

(65) Prior Publication Data
US 2021/0164874 A1 Jun. 3, 2021

(30) Foreign Application Priority Data

Aug. 8, 2017 (JP) .............................. JP2017-153258

(51) Int. Cl.
*G01N 3/48* (2006.01)
(52) U.S. Cl.
CPC ..................... *G01N 3/48* (2013.01)
(58) Field of Classification Search
CPC .. G01N 3/48; G01N 3/00; G01N 3/40; G01N 3/52

USPC ................ 73/12.13, 12.14, 78, 79, 81, 82
See application file for complete search history.

(56) References Cited

U.S. PATENT DOCUMENTS

| 3,435,658 | A | * | 4/1969 | Arthur | ................. | G01M 99/00 |
| | | | | | | 73/12.13 |
| 6,837,094 | B2 | | 1/2005 | Pringle et al. | | |
| 2014/0245819 | A1 | * | 9/2014 | Boitnott | ................. | G01N 3/40 |
| | | | | | | 73/82 |
| 2015/0338327 | A1 | * | 11/2015 | Pittam | ................... | G01N 3/303 |
| | | | | | | 73/12.13 |

FOREIGN PATENT DOCUMENTS

| JP | H06-294724 | 10/1994 |
| JP | 2000-193575 | 7/2000 |
| JP | 2001-133375 | 5/2001 |

(Continued)

OTHER PUBLICATIONS

International Search Report for International Application No. PCT/JP2018/014572 dated Jun. 26, 2018, 4 pages, Japan.

(Continued)

*Primary Examiner* — Robert R Raevis
(74) *Attorney, Agent, or Firm* — Thorpe North & Western (57) ABSTRACT

Provided is a rigidity characteristics measuring device that measures the rigidity characteristics of a golf club head. A head fixing jig holds the golf club head with a face surface facing upward. A linear bushing causes an impact rod to drop vertically toward the golf club head. The impact rod is equipped with an acceleration sensor. A computer calculates the rigidity characteristics, e.g., a CT value, of the golf club head, based on a detected value of the acceleration sensor.

14 Claims, 7 Drawing Sheets

(56) References Cited

FOREIGN PATENT DOCUMENTS

| | | |
|---|---|---|
| JP | 2004-033626 | 2/2004 |
| JP | 2004-317217 | 11/2004 |
| JP | 2008-064599 | 3/2008 |
| JP | 2009-063438 | 3/2009 |
| JP | 2011-240043 | 12/2011 |

OTHER PUBLICATIONS

Technical Description of the Pendulum Test (Revised Version), The Royal and Ancient Golf Club of St Andrews and United States Golf Association, Nov. 2003, 38 pages, United States.

* cited by examiner

RIGIDITY CHARACTERISTICS MEASUREMENT DEVICE

TECHNICAL FIELD

The present technology relates to a rigidity characteristics measuring device that measures the rigidity characteristics of an object to be impacted.

BACKGROUND ART

In the related art, there is known a technique for measuring the rigidity characteristics such as a CT (characteristic time) value and a coefficient of restitution as an indicator that affects rebounding performance of a striking tool such as a golf club head.

In particular, for a golf club for competitive use, a CT value measured by a pendulum test defined by the United States Golf Association (USGA) is used as an evaluation reference value of the rigidity characteristics. The procedure and the like of the pendulum test are described in detail in "Technical Description of the Pendulum Test (Revised Version)", The Royal and Ancient Golf Club of St Andrews and the United States Golf Association, November 2003.

U.S. Pat. No. 6,837,094 describes an apparatus for performing the pendulum test above, in which a golf club the head and the shaft of which are integrated is fixed, and a metallic spherical body on a pendulum strikes the face surface. The spherical body is equipped with an acceleration sensor, and a parameter indicating the rigidity characteristics is calculated from a detected value of the acceleration sensor.

Japan Unexamined Patent Publication No. 2004-33626 describes a method of striking a face surface of a golf club head with an impact hammer and, using a computer, measuring a time at which the acceleration of the impact hammer first decreases to zero immediately after striking. The measured time is then determined for each measurement position, and a distribution of the times is determined to get a rigidity distribution of the golf club head. This enables the rigidity distribution of the golf club head to be measured easily and accurately.

U.S. Pat. No. 6,837,094 is based on the premise that a club shape in which a head and a shaft are integrated is used in a test, so that the test needs to be performed by holding a shaft portion. This causes a problem in that a step of attaching a shaft is required to perform measurement for quality control in a manufacturing process of a head, for example, and the step is cumbersome.

The shaft has a cylindrical shape, and thus is liable to rotate in its circumferential direction. This makes it difficult to set an impact angle with the impactor to be maintained in a constant manner during the test. In addition, the rigidity characteristics may change due to the influence of inherent vibration of the shaft, derived from a material of the shaft, a clamping position, a clamping strength, and the like.

Further, an impact method using a pendulum as in U.S. Pat. No. 6,837,094 makes it difficult to stably strike the lowermost point due to the characteristics of the head shape, such as difference in FP value, etc.). This difference may make a striking position and an impact angle to vary and also makes adjustment difficult.

Japan Unexamined Patent Publication No. 2004-33626 described above is also based on the premise that a club shape in which a head and a shaft are integrated is used in a test and thus has a problem similar to that of U.S. Pat. No. 6,837,094.

SUMMARY

The present technology measures the rigidity characteristics of an object to be impacted easily and accurately.

A rigidity characteristics measuring device according to a first aspect of the technology is configured to measure the rigidity characteristics of an object to be impacted, the rigidity characteristics measuring device including: a holding mechanism that holds the object to be impacted, with a surface to be measured facing upward; a dropping mechanism that causes an impactor to drop in a vertical direction toward the object to be impacted; an acceleration sensor attached to the impactor; and a characteristics calculating unit that calculates the rigidity characteristics of the object to be impacted, based on a detection value of the acceleration sensor.

The rigidity characteristics measuring device according to a second aspect of the technology is configured such that the impactor is formed in a columnar shape with a bottom surface that strikes the object to be impacted and that is formed in a spherical surface shape, and the dropping mechanism causes the impactor to drop along a longitudinal direction of the columnar shape.

The rigidity characteristics measuring device according to a third aspect of the technology is configured such that the dropping mechanism further includes a stopper mechanism that holds the impactor movable in the vertical direction, the stopper mechanism regulating an uppermost position and a lowermost position of the impactor held by the dropping mechanism.

The rigidity characteristics measuring device according to a fourth aspect of the technology further includes a re-impact preventing mechanism that holds the impactor above the surface to be measured after the impactor strikes the surface to be measured, preventing the impactor from re-striking the surface to be measured.

The rigidity characteristics measuring device according to a fifth aspect of the technology further includes: a drop distance adjustment mechanism that adjusts a distance between a dropping start position of the impactor and a surface to be impacted of the object to be impacted.

The rigidity characteristics measuring device according to a sixth aspect of the technology is configured such that at least one of the holding mechanism or the dropping mechanism is movable in a horizontal direction, and a drop position of the impactor on the surface to be measured of the object to be impacted is adjustable.

The rigidity characteristics measuring device according to a seventh aspect of the technology is configured such that the holding mechanism is formed with a damping material that attenuates vibration of the object to be impacted.

The rigidity characteristics measuring device according to an eighth aspect of the technology is configured such that the object to be impacted is a golf club head, and the characteristics calculating unit calculates a CT value of the golf club head.

The rigidity characteristics measuring device according to a ninth aspect of the technology is configured such that the holding mechanism includes a fitting hole formed in a form identical to that of a side portion of the golf club head, and the fitting hole allows the golf club head separated from a shaft to be fitted, with a face surface facing upward, the face surface being the surface to be measured.

According to the first aspect of the technology, the impactor is caused to drop in the vertical direction toward the object to be impacted, so that an impact position and an impact angle of the impactor can be easily maintained in a constant manner, and thus it is advantageous for improving the measurement accuracy of rigidity characteristics.

According to the second aspect of the technology, the impactor is formed in a columnar shape that helps a path of movement along the longitudinal direction is easily restricted to further facilitate maintaining an impact position and an impact angle of the impactor, and thus it is advantageous for further improving the measurement accuracy of the rigidity characteristics. In addition, the impactor has the bottom surface (impacting surface) formed in a spherical surface shape, so the measurement in accordance with a pendulum test can be performed.

According to the third aspect of the technology, there is provided the stopper mechanism that regulates the uppermost position and the lowest position of the impactor, so the drop distance of the impactor can be maintained constant, and thus it is advantageous in terms of maintaining a constant impact velocity on the surface to be impacted.

According to the fourth aspect of the technology, there is provided the re-impact preventing mechanism that prevents the impactor from re-striking the surface to be measured, so it is advantageous for reducing influence on measurement due to repeated impacts in a short time. In addition, the impactor is held above the surface to be measured, so the work efficiency when the object to be impacted of a measurement object is replaced can be improved, and the surface to be measured can be prevented from being scratched, or the like.

According to the fifth aspect of the technology, there is provided the drop distance adjustment mechanism that adjusts the distance (drop distance of the impactor) between the dropping start position of the impactor and the surface to be impacted of the object to be impacted, so the impact velocity of the impactor can be adjusted to a freely selectable velocity, and particularly, the convenience of measuring velocity-dependent rigidity characteristics can be improved.

According to the sixth aspect of the technology, the drop position of the impactor on the surface to be measured of the object to be impacted is adjustable, so the rigidity characteristics at a freely selectable position on the surface to be measured can be measured.

According to the seventh aspect of the technology, the holding mechanism is formed with a damping material, so it is advantageous for preventing the detection value of the acceleration sensor from having excessive noise to perform a stable measurement.

According to the eighth aspect of the present technology, the CT value important for an evaluation indicator of a golf club head can be measured easily with high accuracy.

According to the ninth aspect of the technology, the holding mechanism is formed with the fitting hole formed in a form identical to that of the side portion of the golf club head, so the golf club head can be easily positioned by simply fitting the golf club head to be measured in the fitting hole. In addition, only a golf club head on which no shaft is attached is used as an object to be impacted, so the CT value can be easily measured in a process of prototyping or manufacturing the golf club head.

DETAILED DESCRIPTION

Hereinafter, a rigidity characteristics measuring device according to preferred embodiments of the present technology will be described in detail with reference to the accompanying drawings.

The rigidity characteristics measuring device is configured to measure the rigidity characteristics of an object to be impacted. In the present embodiment, an object to be impacted is a golf club head 30, and a CT value of the golf club head 30 is measured as the rigidity characteristics.

First, the golf club head 30 being an object to be impacted will be described.

Figure 2:
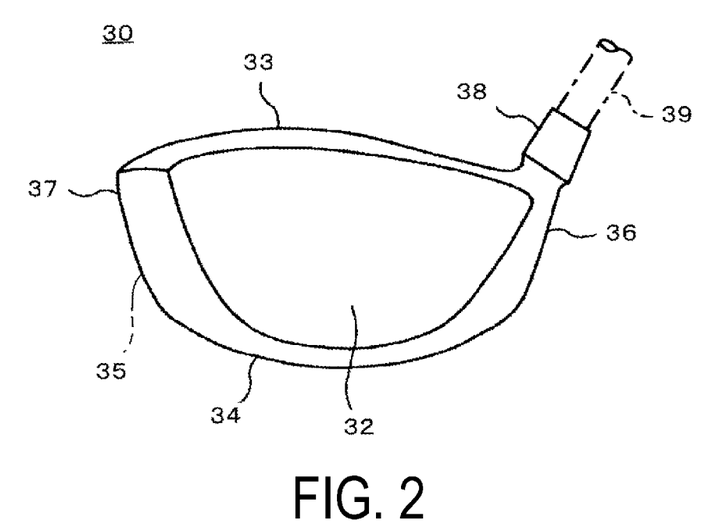
FIG. 2 is a diagram illustrating a structure of a golf club head 30.

As illustrated in FIG. 2, the golf club head 30 includes a face surface 32, a crown portion 33, a sole portion 34, and a side portion 35 to form a hollow structure.

The face surface 32 forms a face surface for striking a golf ball.

The crown portion 33 is connected to the face surface 32.

The sole portion 34 is connected to the face surface 32 and the crown portion 33.

The side portion 35 is connected to the crown portion 33 and the sole portion 34 and faces the face surface 32.

The golf club head 30 is made of metal, for example, and a type of metal having high strength and low specific gravitational force, such as a titanium alloy or an aluminum alloy, is preferably used.

The crown portion 33 is provided with a hosel 38 connecting to a shaft 39 at a position close to the face surface 32 and near a heel 36.

When the face surface 32 is viewed from the front, a toe 37 is on the opposite side of the heel 36 of the golf club head 30.

While the present embodiment is described using a wood-type golf club head having a hollow structure as illustrated in FIG. 2, the present technology is not limited thereto, and the present technology can be applied to an iron-type golf club head having a solid structure.

Figure 1:
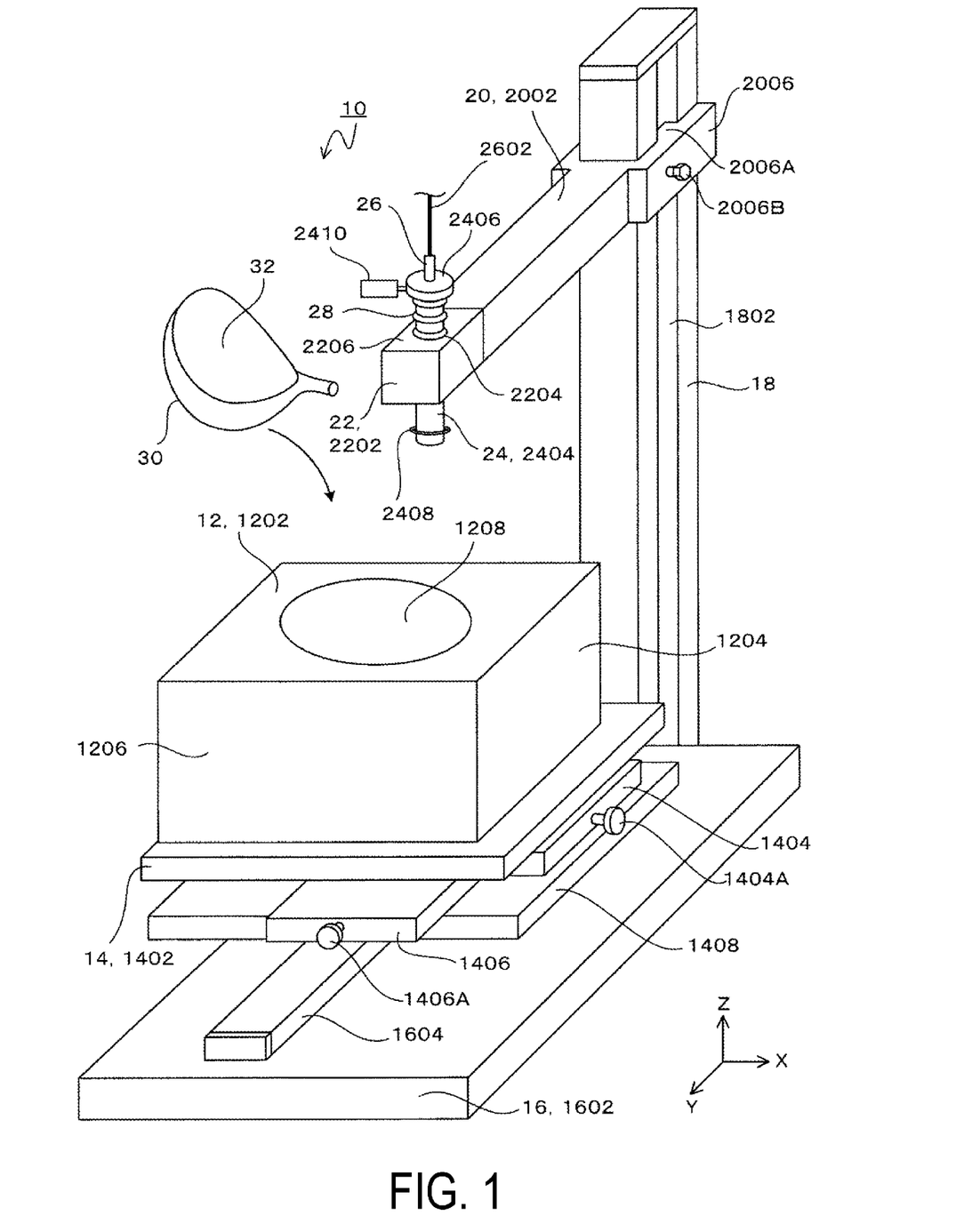
FIG. 1 is an explanatory diagram illustrating a configuration of a rigidity characteristics measuring device 10 according to an embodiment.

FIG. 1 is an explanatory diagram illustrating a configuration of a rigidity characteristics measuring device 10 according to an embodiment.

Figure 6:
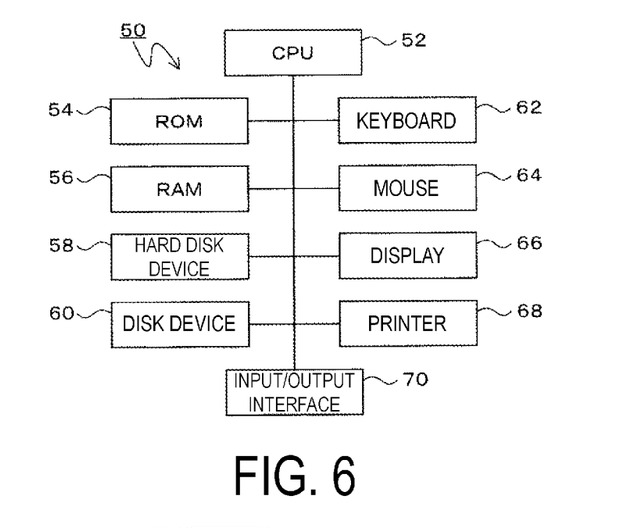
FIG. 6 is a block diagram illustrating a configuration of a computer 50.

The rigidity characteristics measuring device 10 includes a head fixing jig 12, an XY stage 14, a pedestal 16, a supporting column 18, an arm 20, a linear bushing 22, an impact rod 24, an acceleration sensor 26, and a computer 50 (refer to FIG. 6).

The head fixing jig 12 functions as a holding mechanism for holding an object to be impacted, with its surface to be measured facing upward. In the present embodiment, the head fixing jig 12 in a rectangular parallelepiped shape includes an upper surface 1202 facing the impact rod 24 disposed above, a lower surface (not illustrated) in contact with the XY stage 14, a side surface 1204 facing a horizontal direction (X-direction) on the page, and a side surface 1206 facing a depth direction (Y-direction) on the page.

Figure 3:
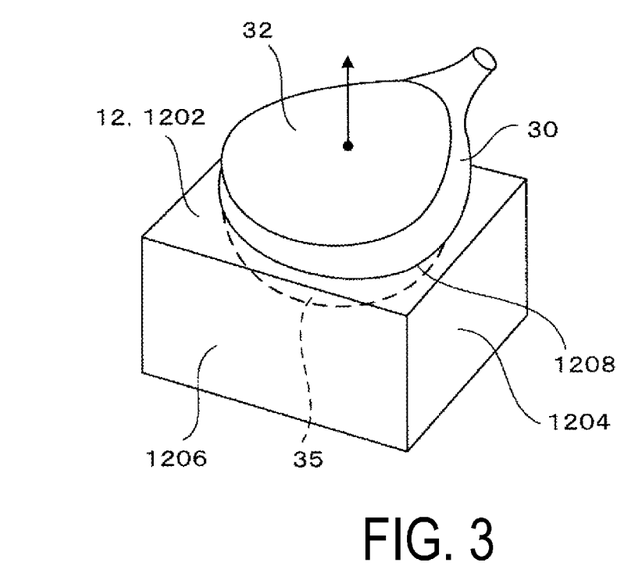
FIG. 3 is a diagram illustrating a state in which a golf club head 30 is set in a head fixing jig 12.

The upper surface 1202 is formed with a fitting hole 1208 into which the golf club head 30 fits. The fitting hole 1208 is formed in the same form as that of the side portion 35 of the golf club head 30, and the golf club head 30 can be fitted thereinto, with the face surface 32 (surface to be measured) facing upward as illustrated in FIG. 3. The golf club head 30 fitted into the fitting hole 1208 is held by the head fixing jig 12 with the face surface 32 facing upward. The fitting hole 1208 is formed in a shape in which at this time, the face surface 32 is substantially horizontal, i.e., a normal line at a face center is the vertical direction. When a golf club head 30 having a different model number (shape) is measured, the head fixing jig 12 is replaced with that formed in accordance with the shape of the golf club head 30.

The head fixing jig 12 is formed of a damping material such as silicon. This is because vibration of the golf club head 30, caused when the impact rod 24 described below strikes the face surface 32, is attenuated to reduce the measured noise of the acceleration sensor 26. In other words, the head fixing jig 12 serving as a holding mechanism is formed containing a damping material that attenuates vibration of the golf club head 30 being an object to be impacted.

The XY stage 14 includes a movable table 1402, an X-axis direction adjustment unit 1404, a Y-axis direction adjustment unit 1406, and a base 1408.

The movable table 1402 is mounted with the head fixing jig 12.

The X-axis direction adjustment unit 1404 includes an X-axis direction operation mechanism and an X-axis direction movement mechanism. When a knob 1404A constituting the X-axis direction operation mechanism is rotated, the X-axis direction movement mechanism is actuated to move the movable table 1402 in the X-axis direction.

The Y-axis direction adjustment unit 1406 includes a Y-axis direction operation mechanism and a Y-axis direction movement mechanism. When a knob 1406A constituting the Y-axis direction operation mechanism is rotated, the Y-axis direction movement mechanism is actuated to move the movable table 1402 in the Y-axis direction.

The Y-axis direction adjustment unit 1406, the X-axis direction adjustment unit 1404, and the movable table 1402 are disposed on an upper surface of the base 1408. In addition, on a bottom surface of the base 1408, rail receivers (not illustrated) that fit with rails 1604 of the pedestal 16 described below are formed.

The mechanism of the XY stage 14 is not limited to the above, and various known mechanisms can be employed.

In the present embodiment, the XY stage 14 enables not only the head fixing jig 12 (the holding mechanism) to move in the horizontal direction (XY direction), but also a drop position of the impact rod 24 (impactor) to be adjusted on the face surface 32 (surface to be measured) of the golf club head 30 (object to be impacted).

The drop position of the impact rod 24 (impactor) on the face surface 32 (surface to be measured) of the golf club head 30 (object to be impacted) may be adjusted by allowing the linear bushing 22 (dropping mechanism) described below to be moved in the horizontal direction (XY direction).

The pedestal 16 includes a bottom plate portion 1602 and the rails 1604.

The bottom plate portion 1602 is disposed on a stable horizontal surface, such as a workbench.

The rails 1604 are disposed on the bottom plate portion 1602 along the Y-axis direction, and the base 1408 of the XY stage 14 is disposed on the rails 1604. The base 1408 of the XY stage 14 is movable on the rails 1604 in the depth direction (Y-axis direction) on the page.

The rails 1604 have a magnet (position fixing mechanism) that is not illustrated and attached to a terminal portion on a back side on the page (supporting column 18 side). In the present embodiment, the base 1408 of the XY stage 14 is made of metal such as stainless steel. When the base 1408 moves to the terminal portion (measuring position) on the back side of the rails 1604 on the page, the base 1408 is attracted to the magnet to cause the position of the XY stage 14 to be fixed.

The supporting column 18 erected vertically (in the Z-axis direction) upward from an end of the bottom plate portion 1602.

The arm 20 includes an arm body 2002 and a position fixing mechanism 2006. The arm body 2002 and the position fixing mechanism 2006 are connected to each other.

The arm body 2002 extends from the supporting column 18 in the horizontal direction (Y-axis direction) toward a front surface of the device (a side on which the XY stage 14 and the like are disposed).

The position fixing mechanism 2006 includes a protrusion 2006A that fits into a groove 1802 provided in the supporting column 18; and a bolt 2006B.

The protrusion 2006A is coupled to the groove 1802 in a vertically movable manner to allow the arm body 2002 and the position fixing mechanism 2006 to move in the vertical direction (Z-axis direction) along the supporting column 18.

The bolt 2006B presses a side surface of the supporting column 18 by being rotationally operated to fix the arm body 2002 and the position fixing mechanism 2006 to the supporting column 18 in an immovable manner. Releasing the bolt 2006B from pressing the side surface of the supporting column 18 enables the arm body 2002 and the position fixing mechanism 2006 to move in the vertical direction along the supporting column 18.

The position fixing mechanism 2006 allows the arm body 2002 to move in the vertical direction and in turn allows the linear bushing 22 connected to the arm body 2002 to move in the vertical direction. This enables a distance in the vertical direction to be adjusted, between a dropping start position of the impact rod 24 (impactor) described below and the face surface 32 (surface to be impacted) of the golf club head 30 (object to be impacted). In other words, the position fixing mechanism 2006 functions as a drop-distance adjustment mechanism.

The distance in the vertical direction between the dropping start position of the impact rod 24 and the face surface 32 can be adjusted as described above, such that the impact velocity of the impact rod 24 on the face surface 32 changes according to the distance. The CT value to be measured in the present embodiment is known to be velocity dependent. Thus, the impact velocity of the impact rod 24 on the face surface 32 is predetermined, and measurement needs to be performed at the impact velocity. Providing the drop-distance adjustment mechanism enables adjusting the impact velocity of the impact rod 24 on the face surface 32 as desired.

The linear bushing 22 is attached to a leading end of the arm body 2002 of the arm 20 and functions as a dropping mechanism that causes the impact rod 24 (impactor) to drop in the vertical direction (longitudinal direction of the impact rod 24 in a columnar shape) toward the golf club head 30 (object to be impacted).

The linear bushing 22 includes a body portion 2202 and an insertion hole 2204. The insertion hole 2204 passes through a lower surface 2208 from an upper surface 2206 of the body portion 2202 (refer to FIG. 5). Steel balls constituting a bearing mechanism are disposed in an inner circumferential surface of the insertion holes 2204 in the body portion 2202 to guide the impact rod 24 inserted into the insertion hole 2204 vertically downward.

Using the linear bushing 22 regulates a drop direction of the impact rod 24, so a drop position on the golf club head 30 can be adjusted with high accuracy.

As the linear bushing 22, a simple cylindrical slider may be used.

Figure 4:
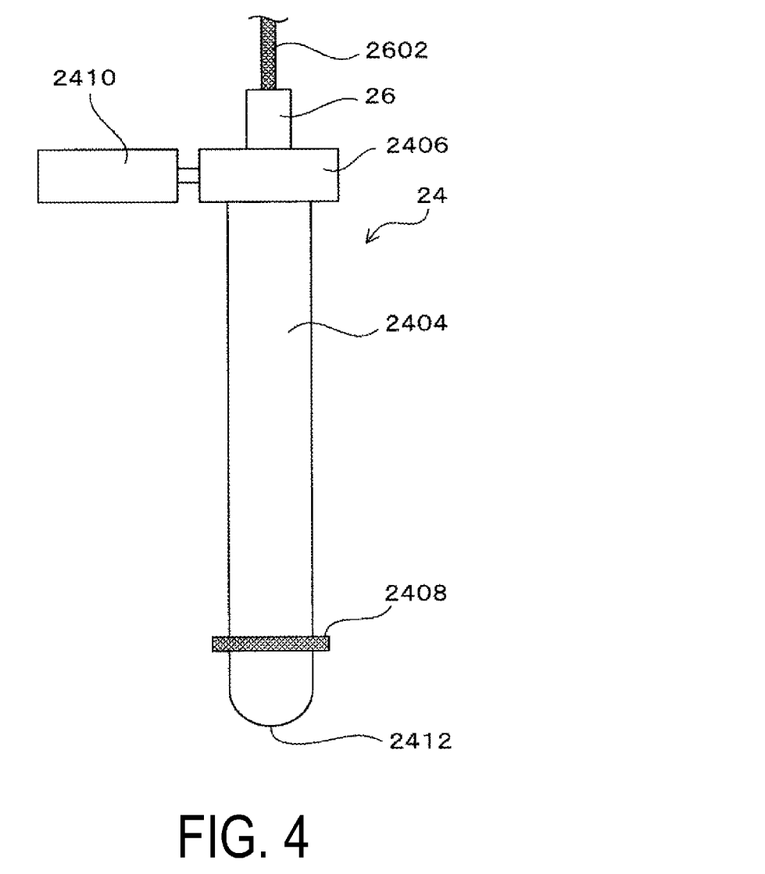
FIG. 4 is a diagram illustrating a structure of an impact rod 24.

As illustrated in FIG. 4, the impact rod 24 (impactor) includes a rod body 2404, an upper stopper 2406, a lower stopper 2408, and an operating lever 2410.

The rod body 2404 is a cylindrical rod-like member and is made of metal such as stainless steel. The rod body 2404 may have a column shape other than a cylindrical column (e.g., a prism shape or the like). The rod body 2404 has a bottom surface 2412 (bottom surface on a side striking the golf club head 30 (object to be impacted) in a use state) that is formed in a spherical shape. The rod body 2404 is formed having a diameter that allows the rod body 2404 to drop out of the insertion hole 2204 of the linear bushing 22.

The upper stopper 2406 is attached to an upper end portion (end portion opposite the bottom surface 2412) of the rod body 2404. The upper stopper 2406 has an outer diameter greater than an inner diameter of the insertion hole 2204 of the linear bushing 22, so that the upper stopper 2406 cannot go through the insertion hole 2204 of the linear bushing 22. Thus, when the impact rod 24 is dropped, the impact rod 24 cannot move downward from a position where the upper stopper 2406 comes into contact with the upper surface 2206 of the linear bushing 22. In other words, the upper stopper 2406 regulates a lowermost position of the impact rod 24 positioned in the insertion hole 2204 of the linear bushing 22.

In actual use, as illustrated in FIGS. 1 and 5, a spring 28 is interposed between the upper stopper 2406 and the upper surface 2206 of the linear bushing 22, such that the upper stopper 2406 and the upper surface 2206 do not directly come into contact with each other. The spring 28 is a compression coil spring, for example, and the rod body 2404 of the impact rod 24 is inserted into an inner diameter side of the spring 28.

As described in detail below, the spring 28 functions as a re-impact preventing mechanism that holds the impact rod 24 above the face surface 32 after the impact rod 24 (impactor) strikes the face surface 32 (surface to be measured), preventing the impact rod 24 (impactor) from re-striking the face surface 32.

The lower stopper 2408 is attached close to the bottom surface 2412 of the rod body 2404.

The lower stopper 2408 is formed of a flexible member and is made of rubber, for example.

The lower stopper 2408 has an outer diameter greater than the inner diameter of the insertion hole 2204 of the linear bushing 22, such that the lower stopper 2408 also cannot go through the insertion hole 2204 of the linear bushing 22. Thus, when the impact rod 24 is moved upward, the impact rod 24 cannot move upward from a position where the lower stopper 2408 comes into contact with the lower surface 2208 of the linear bushing 22. In other words, the lower stopper 2408 regulates an uppermost position of the impact rod 24 positioned in the insertion hole 2204.

In addition, the lower stopper 2408 is detachable from the rod body 2404. To remove the impact rod 24 from the linear bushing 22, the lower stopper 2408 is removed from the rod body 2404, and then the rod body 2404 is moved upward to be pulled out from the insertion hole 2204. Then, to attach the impact rod 24 to the linear bushing 22, the rod body 2404 having the lower stopper 2408 removed is inserted into the insertion hole 2204, and then the rod body 2404 is moved downward to a position regulated by the spring 28. After that, the lower stopper 2408 is attached to the rod body 2404.

In other words, as described above, the linear bushing 22 (dropping mechanism) holds the impact rod 24 (impactor) in a vertically movable manner, and the upper stopper 2406 and the lower stopper 2408 each function as a stopper mechanism for regulating the uppermost position and the lowermost position of the impact rod 24 inserted (held) in the linear bushing 22.

The operating lever 2410 is a rod-like member attached to the upper stopper 2406 and is used by a measurer to move the impact rod 24 to an upward position (refer to FIG. 5). More specifically, after holding the operating lever 2410 to lift the impact rod 24 upward, a measurer releases the operating lever 2410 to allow the impact rod 24 to free fall.

The impact rod 24 preferably has a size such as the rod body 2404 having a diameter of 12 mm or more and 20 mm or less; and a length (length from a boundary between the upper stopper 2406 and the acceleration sensor 26 to the bottom surface 2412) of 60 mm or more and 120 mm or less and preferably also has a mass (including the rod body 2404, the upper stopper 2406, the lower stopper 2408, and the operating lever 2410) of 100 g or more and 200 g or less; and a radius of curvature of the bottom surface 2412 of 30 mm or less, more preferably 20 mm or more and 30 mm or less.

This is because the impactor defined in the pendulum impact test procedure (refer to Non-Patent Document 1) has a size within the range described above.

The acceleration sensor 26 is attached to a surface of the impact rod 24 (impactor), opposite the bottom surface 2412, to measure the acceleration of the impact rod 24, which is caused when the impact rod 24 strikes the face surface 32 (object to be impacted).

The acceleration sensor 26 is connected to the computer 50 using a wire 2602 via a digital oscilloscope and outputs a detected value to the computer 50. In the digital oscilloscope, an analog signal output from the acceleration sensor is converted to a digital value. The acceleration sensor 26 and the computer 50 may be connected via wireless communication.

FIG. 6 is a block diagram illustrating a configuration of the computer 50.

The computer 50 includes a CPU (Central Processing Unit) 52; and a ROM (Read Only Memory) 54, a RAM (Random Access Memory) 56, a hard disk device 58, a disk device 60, a keyboard 62, a mouse 64, a display 66, a printer 68, an input/output interface 70, and the like, connected via an interface circuit and a bus line, which are not illustrated.

The ROM 54 stores a control program, and the RAM 56 provides a working area.

The hard disk device 58 stores a rigidity characteristics calculation program that calculates the rigidity characteristics (CT values in the present embodiment) of the golf club head 30 (object to be impacted) based on a detection value of the acceleration sensor 26.

The disk device 60 records and/or plays data on a recording medium such as a CD (Compact Disc) or a DVD (Digital Video Disc).

The keyboard 62 and the mouse 64 accept input via operations by an operator.

The display 66 displays and outputs data, the printer 68 prints data and outputs data, and thus data is output using the display 66 and the printer 68.

The input/output interface 70 transmits data to and receives data from an external device, such as the acceleration sensor 26.

Next, with reference to the flowchart of FIG. 7, a measurement procedure using the rigidity characteristics measuring device 10 will be described.

Figure 7:
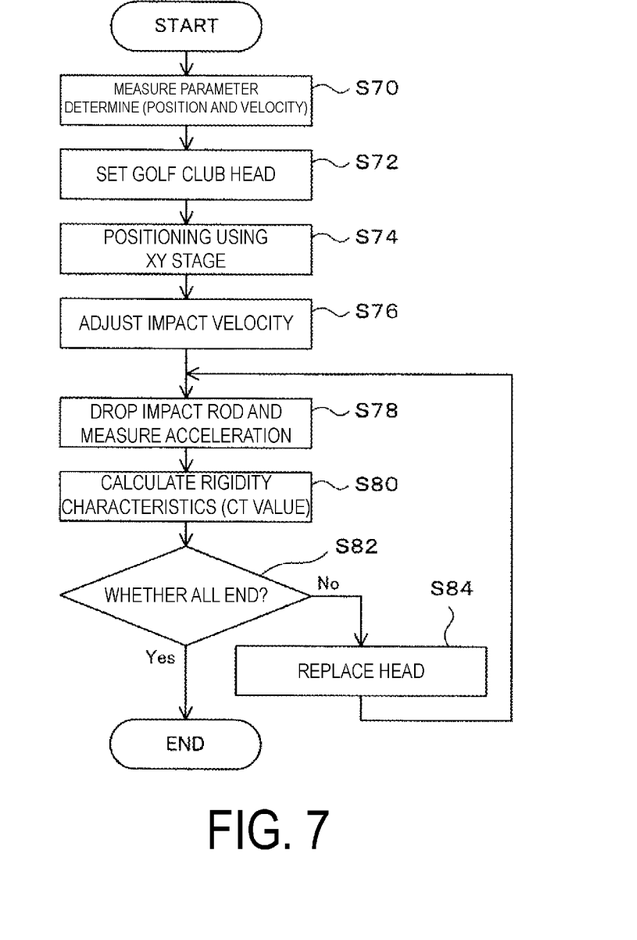
FIG. 7 is a flowchart illustrating a measurement procedure with a rigidity characteristics measuring device 10.

In the flowchart of FIG. 7, the plurality of mass-produced golf club heads 30 of an identical model is prepared and the rigidity characteristics (e.g. a CT value) of each of the golf club heads 30 are measured.

Prior to measurement, measurement parameters such as a measurement position of the rigidity characteristics (impact position of the impact rod 24 on the face surface 32) and an impact velocity of the impact rod 24 are determined (step S70).

Next, the golf club head 30 is set in the head fixing jig 12 (step S72).

More specifically, a measurer first causes the XY stage 14 on the rails 1604 to move in a forward direction. This is to move the head fixing jig 12 to a position where it does not interfere with the linear bushing 22 and the like when the golf club head 30 is set. Subsequently, with the face surface 32 of the golf club head 30 facing upward, the side portion 35 thereof is fitted into the fitting hole 1208. Then, the XY stage 14 on the rails 1604 is moved in the back direction (toward the supporting column 18). When the XY stage 14 moves back to an end portion of each of the rails 1604, the magnet fixes the XY stage 14 to the position thereof.

Subsequently, the XY stage is operated to align a measurement position on the face surface 32 and a drop position of the impact rod 24 such that the positions coincide with each other (step S74).

In addition, a position of the arm 20 with respect to the supporting column 18 is adjusted to adjust the impact velocity of the impact rod 24 on the face surface 32 (step S76). In other words, when the impact rod 24 free falls toward the face surface 32, its impact velocity varies in accordance with a dropping start position of the impact rod 24. Thus, for example, the acceleration is measured by actually causing the impact rod 24 to strike the face surface 32. Then, the acceleration is integrated to calculate the impact velocity. When the impact velocity is more than the impact velocity determined in step S70, a position of the arm 20 is adjusted to be raised. When the impact velocity is less than that, the position of the arm 20 is adjusted to be lowered.

As described below (refer to FIG. 5), the impact rod 24 strikes the face surface 32, compressing the spring 28. When the position of the arm 20 is raised and a distance between the dropping start point of the impact rod 24 and the face surface 32 is increased, the spring 28 is greatly compressed at the time of impact, and the impact rod 24 decreases in impact velocity compared to a previous position change of the arm 20. When the position of the arm 20 is raised excessively, the impact rod 24 and the face surface 32 do not come into contact with each other.

In addition, when the position of the arm 20 is lowered and the distance between the dropping start point of the impact rod 24 and the face surface 32 is shortened, the impact rod 24 strikes the face surface 32 with a small amount of compression of the spring 28 (before deceleration). This causes the impact rod 24 to increase in impact velocity compared to a previous position change of the arm 20. When the position of the arm 20 is lowered excessively, the impact rod 24 and the face surface 32 come into contact with each other even when unloaded.

Subsequently, the impact rod 24 is caused to drop onto the face surface 32, and the acceleration at the time of impact is measured by the acceleration sensor 26 (step S78).

FIG. 5 is a diagram schematically illustrating the behavior of the impact rod 24 during measurement.

Figure 5A:
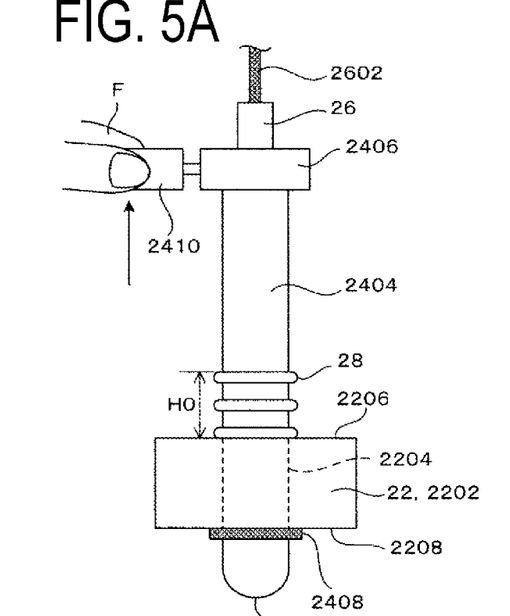
FIG. 5 is an explanatory diagram illustrating the behavior of an impact rod 24 during impact.

First at the time of measurement, as illustrated in FIG. 5A, a measurer holds the operating lever 2410 and pulls upward the impact rod 24. When the impact rod 24 is pulled up by a predetermined amount, the lower stopper 2408 comes into contact with the lower surface 2208 of the linear bushing 22, and then the impact rod 24 cannot further move upward.

During the measurement, the spring 28 is inserted onto the rod body 2404 of the impact rod 24. The spring 28 is positioned on the upper surface 2206 of the linear bushing 22. In the state of FIG. 5A, the spring 28 is not subject to force, so that the spring 28 has a natural length H0.

Figure 5B:
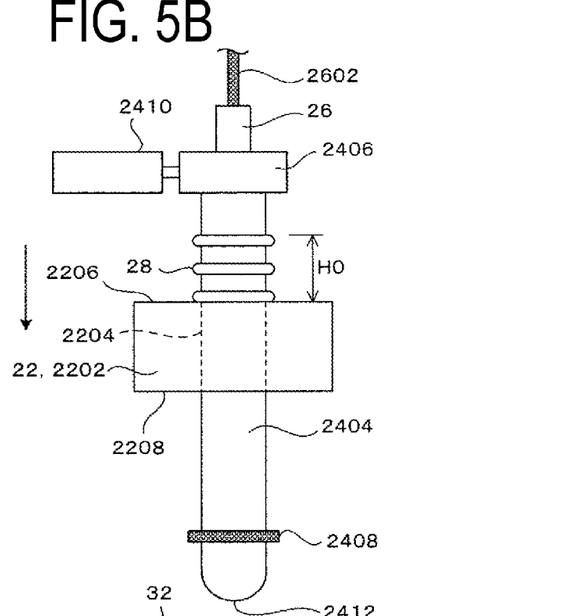
Figure 5C:
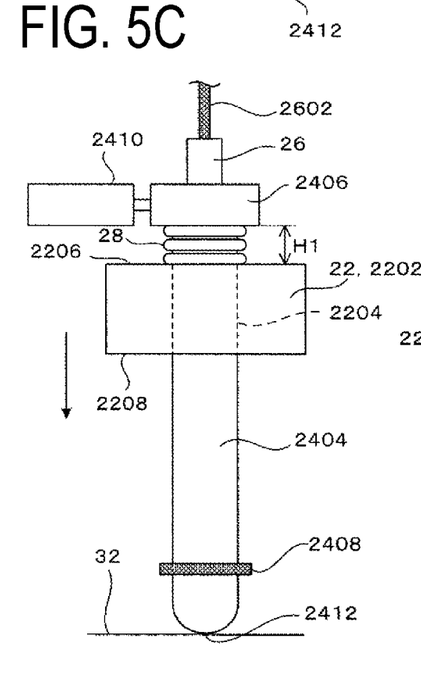

Subsequently, turning on the acceleration sensor 26 (measurement start), the measurer releases the operating lever 2410 to cause the impact rod 24 to drop in the vertical direction. As illustrated in FIG. 5B, the impact rod 24 free falls, and the falling velocity is accelerated by gravitational acceleration.

After that, when the upper stopper 2406 drops to an upper end position of the spring 28, a load (mass×acceleration) of the impact rod 24 is applied to the spring 28. This load causes the spring 28 to contract to a length H1 that is shorter than the natural length H0 (refer to FIG. 5C). Then, a reaction force from the spring 28 is applied to the impact rod 24, and the falling velocity is reduced. During this deceleration, the impact rod 24 strikes the face surface 32 at a predetermined impact velocity.

The impact rod 24 having impacted on the face surface 32 moves upward due to a reaction force received. When the impact rod 24 moves upward, no load is applied to the spring 28, and then the spring 28 returns to the natural length H0. After moving upward by a certain distance, the impact rod 24 falls downward (toward the face surface 32) again due to gravitational force. However, the dropping start position is lower than that of the initial drop, so the load applied to the spring 28 decreases, and thus the load on the spring 28 does not reach the level that causes the spring 28 to contract (or the amount of contraction decreases compared to FIG. 5C).

Figure 5D:
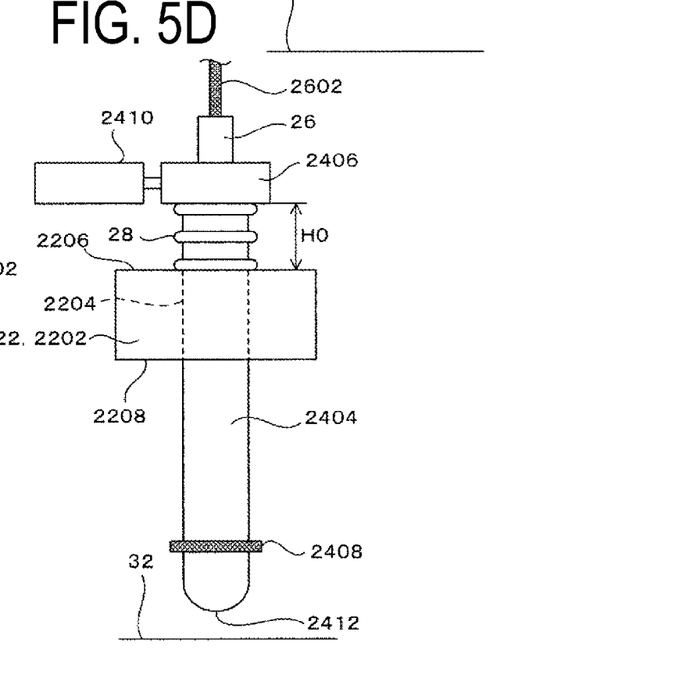

Accordingly, as illustrated in FIG. 5D, the bottom surface 2412 of the impact rod 24 is held above the face surface 32. In other words, the spring 28 functions as the re-impact preventing mechanism that holds the impact rod 24 above the face surface 32, preventing the impact rod 24 from re-striking the face surface 32 after the impact rod 24 (impactor) strikes the face surface 32 (surface to be measured).

The re-impact preventing mechanism described above is provided to prevent noise in a detected value of the acceleration sensor 26 from increasing due to a re-impact.

Returning to the description of FIG. 7, the computer 50 calculates the rigidity characteristics (CT value) of the golf club head 30 using the acceleration detected in step S78 (step S80).

The acceleration detected by the acceleration sensor 26 is time series acceleration data detected at a predetermined sampling interval. The computer 50 filters the acceleration data to remove noise and integrates it and converts it into time series data on velocity V.

Figure 8:
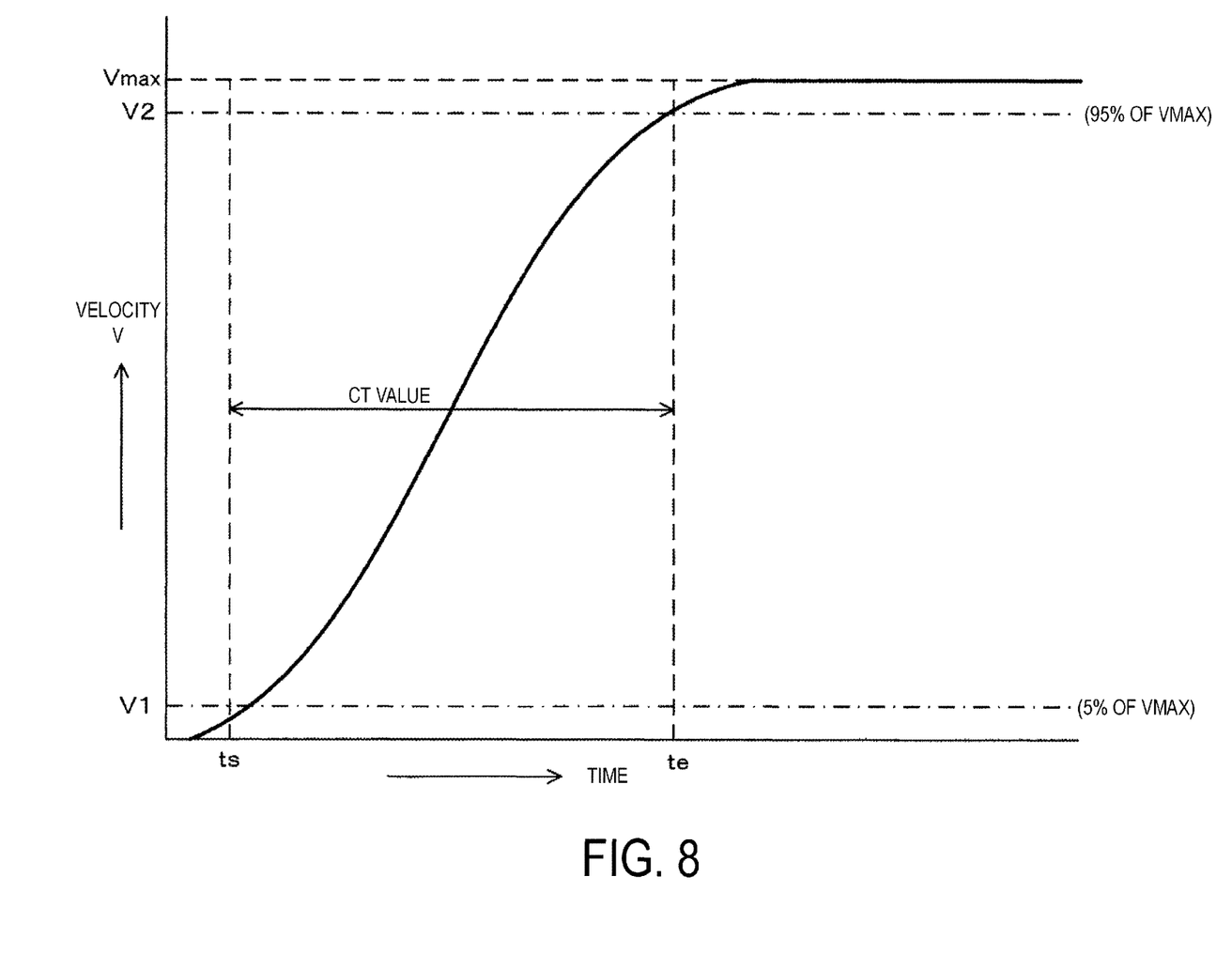
FIG. 8 is a graph showing time series data on velocity V of an impact rod 24.

FIG. 8 is a graph showing time series data on velocity V of the impact rod 24.

As described below, the computer 50 calculates a CT value indicating the rigidity characteristics of the golf club head 30.

A maximum velocity in the time series data on velocity V is denoted as Vmax.

A time at which the velocity V reaches V1 (V1=α % of Vmax) is denoted as start time ts.

A time at which the velocity V reaches V2 (V2=(β % of Vmax) is denoted as end time te.

Then, α is from 0 to 99%, β is from 1 to 100%, and α is less than β.

The CT value is determined as follows: te−ts.

Typically, α is set to 5%, and β is set to 95%.

As described above, the CT value is velocity dependent. Thus, the CT value may be measured at a plurality of impact velocities, and a representative CT value of the golf club head 30 may be calculated from a relationship between the impact velocity and the CT value.

Figure 9:
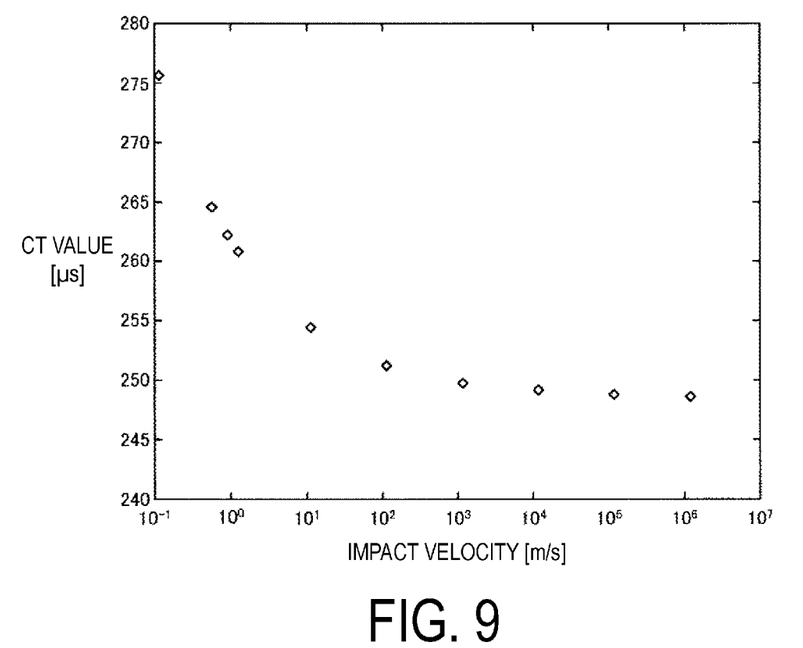
FIG. 9 is a graph showing an example of CT values measured multiple times by changing impact velocity.

FIG. 9 is a graph showing an example of CT values measured multiple times by changing an impact velocity for the identical golf club head 30.

In FIG. 9, the horizontal axis indicates an impact velocity (m/s), and the vertical axis indicates CT values (μs).

As illustrated in the graph of FIG. 9, the CT value increases as the impact velocity decreases, and the CT value decreases as the impact velocity increases.

Figure 10:
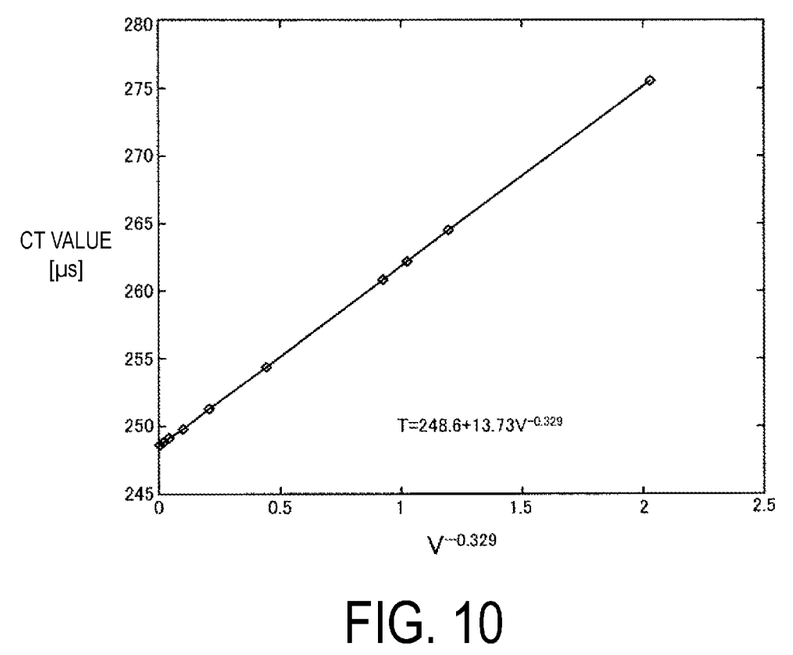
FIG. 10 is a graph obtained by converting FIG. 9.

FIG. 10 is a graph obtained by converting FIG. 9 such that a value in the horizontal axis is a value in FIG. 9 to the power of −0.329 ($V^{-0.329}$).

The conversion described above causes the CT values to align in a straight line. An intersection point (y-intercept) of the straight line and Y-axis is indicated as a representative CT value of the golf club head 30. In the example of FIG. 10, the CT value at each impact velocity is aligned on a line defined as follows: $T=248.6+13.73\ V^{-0.329}$, and a representative CT value is 248.6.

While FIGS. 9 and 10 each illustrate results of measurements performed ten times by changing the impact velocity, a representative CT value of the golf club head 30 is typically calculated by performing measurements approximately three times (three velocity levels).

Returning to the description of FIG. 7, until all of the measurements of the plurality of golf club heads 30 prepared are completed (No at step S82), the golf club head 30 set in the head fixing jig 12 is replaced (step S84), the processing returns to step S78, and the subsequent processing is repeated.

While it is conceivable that the golf club head 30 of an identical model does not basically require the positioning of the impact position (step S74) and the adjustment of the impact velocity (step S76) after the replacement of the golf club head 30, in consideration of factors such as a manufacturing error of the individual golf club head 30 and an error in setting in the head fixing jig 12, the measurement may be performed if necessary after steps S74 and S76 are performed.

Then, when all of the measurements of the plurality of golf club heads 30 prepared have been completed (Yes at step S82), the processing according to the present flowchart ends.

As described above, the rigidity characteristics measuring device 10 according to the embodiment causes the impact rod 24, an impactor, to fall vertically toward the golf club head 30, an object to be impacted. This facilitates maintaining an impact position and an impact angle of the impact rod 24 in a constant manner and has the advantage of improving the measurement accuracy of the rigidity characteristics.

The rigidity characteristics measuring device 10 is configured such that the impact rod 24 is formed in a columnar shape that helps a path of movement along the longitudinal direction to be easily restricted to further facilitate maintaining an impact position and an impact angle of the impact rod 24, and thus it is advantageous for further improving the measurement accuracy of the rigidity characteristics. In addition, the impact rod 24 has the bottom surface 2412 (impacting surface) formed in a spherical surface shape, so the measurement in accordance with a pendulum test can be performed.

The rigidity characteristics measuring device 10 is also configured such that there are provided the upper stopper 2406 and the lower stopper 2408 (stopper mechanism) that regulate the uppermost position and the lowest position of the impact rod 24, so the drop distance of the impact rod 24 can be maintained constant, and thus it is advantageous in terms of maintaining a constant impact velocity on the face surface 32.

The rigidity characteristics measuring device 10 is also configured such that there is provided the spring 28 (re-impact preventing mechanism) that prevents the impact rod 24 from re-striking the face surface 32, so it is advantageous for reducing influence on measurement due to repeated impacts in a short time. In addition, the impact rod 24 is held above the face surface 32, so the work efficiency when the golf club head 30 to be an object to be measured is replaced can be improved, and the face surface 32 can be prevented from being scratched, or the like.

The rigidity characteristics measuring device 10 is also configured such that there is provided the drop distance adjustment mechanism (the position fixing mechanism 2006 of the arm 20) that adjusts the distance (drop distance of the impactor) between the dropping start position of the impact rod 24 and the face surface 32, so the impact velocity of the impact rod 24 can be adjusted to a freely selectable velocity, and particularly, the convenience of measuring velocity-dependent rigidity characteristics can be improved.

The rigidity characteristics measuring device 10 is also configured such that the drop position of the impact rod 24 on the face surface 32 is adjustable, so the rigidity characteristics at a freely selectable position on the face surface 32 can be measured.

The rigidity characteristics measuring device 10 is also configured such that the head fixing jig 12 is formed with a damping material, so it is advantageous for preventing the detection value of the acceleration sensor 26 from having excessive noise to perform a stable measurement.

The rigidity characteristics measuring device 10 also can measure the CT value important for an evaluation indicator of the golf club head 30 easily with high accuracy. In addition, only the golf club head 30 on which no shaft is attached can be used as an object to be impacted, so the CT value can be easily measured in a process of prototyping or manufacturing the golf club head 30.

While in the present embodiment, the CT value is calculated as the rigidity characteristics of the golf club head 30, other rigidity characteristics that can be calculated using the detection value of the acceleration sensor 26, such as a coefficient of restitution (a ratio of relative velocities before and after impact), may be calculated.

The invention claimed is:

1. A rigidity characteristics measuring device configured to measure rigidity characteristics of an object to be impacted, the rigidity characteristics measuring device comprising:
   a fixing jig that holds the object to be impacted, with a surface to be measured facing upward;
   an impactor;
   a linear bushing that causes the impactor to drop in a vertical direction toward the object to be impacted, the linear bushing holding the impactor movable in the vertical direction;
   an acceleration sensor attached to the impactor; and
   a computer that calculates the rigidity characteristics of the object to be impacted, based on a detection value of the acceleration sensor;
   wherein the impactor comprises an upper stopper and a lower stopper, the upper stopper limiting a lower position of the impactor and the lower stopper limiting an upper position of the impactor.

2. The rigidity characteristics measuring device according to claim 1, wherein
   the impactor is formed in a columnar shape with a bottom surface that strikes the object to be impacted and that is formed in a spherical surface shape, and
   the linear bushing causes the impactor to drop along a longitudinal direction of the columnar shape.

3. The rigidity characteristics measuring device according to claim 2, further comprising:
   a spring that holds the impactor above the surface to be measured after the impactor strikes the surface to be measured, preventing the impactor from re-striking the surface to be measured.

4. The rigidity characteristics measuring device according to claim 3, further comprising:
   a vertically slidable adjuster that adjusts a distance between a dropping start position of the impactor and a surface to be impacted of the object to be impacted.

5. The rigidity characteristics measuring device according to claim 4, wherein
   at least one of the fixing jig or the linear bushing is movable in a horizontal direction, and
   a drop position of the impactor on the surface to be measured of the object to be impacted is adjustable.

6. The rigidity characteristics measuring device according to claim 5, wherein the fixing jig is formed with a damping material that attenuates vibration of the object to be impacted.

7. The rigidity characteristics measuring device according to claim 6, wherein
   the object to be impacted is a golf club head, and
   the computer calculates a CT value of the golf club head.

8. The rigidity characteristics measuring device according to claim 7, wherein
   the fixing jig includes a fitting hole formed in a form identical to that of a side portion of the golf club head, and
   the fitting hole allows the golf club head separated from a shaft to be fitted, with a face surface facing upward, the face surface being the surface to be measured.

9. The rigidity characteristics measuring device according to claim 1, further comprising:
   a vertically slidable adjuster that adjusts a distance between a dropping start position of the impactor and a surface to be impacted of the object to be impacted.

10. The rigidity characteristics measuring device according to claim 1, wherein
    at least one of the fixing jig or the linear bushing is movable in a horizontal direction, and
    a drop position of the impactor on the surface to be measured of the object to be impacted is adjustable.

11. The rigidity characteristics measuring device according to claim 1, wherein
    the object to be impacted is a golf club head, and
    the computer calculates a CT value of the golf club head.

12. The rigidity characteristics measuring device according to claim 11, wherein
    the fixing jig includes a fitting hole formed in a form identical to that of a side portion of the golf club head, and
    the fitting hole allows the golf club head separated from a shaft to be fitted, with a face surface facing upward, the face surface being the surface to be measured.

13. A rigidity characteristics measuring device configured to measure rigidity characteristics of an object to be impacted, the rigidity characteristics measuring device comprising:
    a fixing jig that holds the object to be impacted, with a surface to be measured facing upward;
    a linear bushing that causes an impactor to drop in a vertical direction toward the object to be impacted;
    an acceleration sensor attached to the impactor;
    a computer that calculates the rigidity characteristics of the object to be impacted, based on a detection value of the acceleration sensor; and
    a spring that holds the impactor above the surface to be measured after the impactor strikes the surface to be measured, preventing the impactor from re-striking the surface to be measured.

14. A rigidity characteristics measuring device configured to measure rigidity characteristics of an object to be impacted, the rigidity characteristics measuring device comprising:
    a fixing jig that holds the object to be impacted, with a surface to be measured facing upward;
    a linear bushing that causes an impactor to drop in a vertical direction toward the object to be impacted;
    an acceleration sensor attached to the impactor; and
    a computer that calculates the rigidity characteristics of the object to be impacted, based on a detection value of the acceleration sensor;
    wherein the fixing jig is formed with a damping material that attenuates vibration of the object to be impacted.

* * * * *